(12) United States Patent
Zou et al.

(10) Patent No.: US 11,191,790 B2
(45) Date of Patent: Dec. 7, 2021

(54) **BIOLOGICALLY PURE *FAECALIBACTERIUM BUTYRICIGENERANS* STRAIN, COMPOSITION INCLUDING THE SAME AND METHOD FOR TREATING ULCERATIVE COLITIS**

(71) Applicant: BGI SHENZHEN, Shenzhen (CN)

(72) Inventors: Yuanqiang Zou, Shenzhen (CN); Wenbin Xue, Shenzhen (CN); Liang Xiao, Shenzhen (CN); Xiaoping Li, Shenzhen (CN); Jinghong Yu, Shenzhen (CN); Chuan Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 69 days.

(21) Appl. No.: 16/271,104

(22) Filed: Feb. 8, 2019

(65) Prior Publication Data

US 2019/0240265 A1 Aug. 8, 2019

Related U.S. Application Data

(63) Continuation of application No. PCT/CN2016/094846, filed on Aug. 12, 2016.

(51) Int. Cl.
| | |
|---|---|
| *A61K 35/741* | (2015.01) |
| *A61K 9/00* | (2006.01) |
| *A61P 29/00* | (2006.01) |
| *A61P 1/00* | (2006.01) |
| *A23L 33/135* | (2016.01) |
| *C12N 1/20* | (2006.01) |
| *A61K 35/74* | (2015.01) |

(52) U.S. Cl.
CPC .......... *A61K 35/741* (2013.01); *A23L 33/135* (2016.08); *A61K 9/0053* (2013.01); *A61K 35/74* (2013.01); *A61P 1/00* (2018.01); *A61P 29/00* (2018.01); *C12N 1/20* (2013.01)

(58) Field of Classification Search
None
See application file for complete search history.

(56) References Cited

U.S. PATENT DOCUMENTS

2016/0000838 A1* 1/2016 Harmsen ................ A23L 33/15
424/93.3

FOREIGN PATENT DOCUMENTS

| CN | 104413334 | 3/2015 |
|---|---|---|
| CN | 104415060 | 3/2015 |
| CN | 104432001 | 3/2015 |
| CN | 104740138 | 7/2015 |
| WO | 2012142605 | 10/2012 |

OTHER PUBLICATIONS

Miquel, S. et al. Faecalibacterium prausnitzii and human intestinal health. Current Opinion in Microbiology (2013) (16). pp. 255-261. (Year: 2013).*

Martin, Rebeca et al. The Commensal Bacterium *Faecalibacterium prausnitzii* is Protective in DNBS-induced Chronic Moderate and Severe Colitis Models. Inflamm Bowel Dis. vol. 20, No. 3, Mar. 2014. pp. 417-430. (Year: 2014).*

WIPO, ISR for PCT/CN2016/094846, Mar. 20, 2017.

Kumari et al., "Fluctuations in butyrate-producing bacteria in ulcertative colitis patients of North India," World Journal of Gastroenterology, vol. 19, issue 22, Jun. 14, 2013, pp. 3404-3414.

Vital et al., "Revealing the Bacterial Butyrate Synthesis Pathways by Analyzing (Meta)genomic Data," mBio, vol. 5, issue 2, Apr. 22, 2014, pp. 1-11.

* cited by examiner

*Primary Examiner* — Nghi V Nguyen
(74) *Attorney, Agent, or Firm* — Hodgson Russ LLP

(57) ABSTRACT

Provided are a biologically pure *Faecalibacterium butyricigenerans* strain AF52-21 deposited under CGMCC Accession No. 1.5206 and a composition including the same and a carrier. A method for treating an inflammation-related disease in a subject in need thereof is also provided. The *Faecalibacterium butyricigenerans* is useful for treating ulcerative colitis and related disorders.

13 Claims, 3 Drawing Sheets

Specification includes a Sequence Listing.

BIOLOGICALLY PURE *FAECALIBACTERIUM BUTYRICIGENERANS* STRAIN, COMPOSITION INCLUDING THE SAME AND METHOD FOR TREATING ULCERATIVE COLITIS

CROSS-REFERENCE TO RELATED APPLICATIONS

This application is a continuation of International Application No. PCT/CN2016/094846 filed on Aug. 12, 2016, the entire disclosure of which is incorporated herein by reference.

FIELD

The present disclosure relates to the technical field of microorganisms, in particular to a biologically pure *Faecalibacterium butyricigenerans* strain, a composition including the same and a method for treating an inflammation-related disease.

BACKGROUND

A large number of symbiotic microflora, resident in the human intestinal tract (with the total cell number 10 times than that of human cells) and constituting the "second organ" of the human body, not only participate in digestion and absorption of nutrients in the host, but also play an important role in maintenance of human health. Firmicutes and Bacteroidetes are two predominant microflora among them. It has been demonstrating in more and more literatures that a strong correlation exists between diverse compositions of the intestinal microflora and occurrence of various diseases, such as obesity, diabetes, irritable bowel syndrome, ulcerative enteritis, colon cancer and fatty liver. Destruction of intestinal microflora balance under the healthy status by environment, diet or drugs will lead to intestinal dysfunction, thus causing onset of the above diseases.

Ulcerative colitis (UC) is one of inflammatory bowel diseases (IBD). Although lacking clear pathogenesis, it is generally acknowledged in clinic as a result of an immune response triggered by abnormal intestinal microflora in a genetically susceptible individual with clinical manifestations of abdominal pain, diarrhea, mucosanguineous feces and the like, as reported in many domestic and foreign researches.

At present, the commonly-used drug for treating UC includes aminosalicylic acid preparations (such as sulfasalazine, SASP), glucocorticoids and immunosuppressive agents, which alleviate the disease by inhibiting inflammation and immune response. However, these drugs also bring with disadvantages like requirement of long time period for controlling the disease, obvious side effects, high incidence of recurrence and impossible eradication.

SUMMARY

Embodiments of the present disclosure aim at to solve at least one of the problems existing in the related art, or to provide at least a commercial choice.

Therefore, the present disclosure provides in embodiments a biologically pure *Faecalibacterium butyricigenerans* strain AF52-21, a composition including the biologically pure *Faecalibacterium butyricigenerans* strain AF52-21 and a carrier, wherein the composition is capable of treating an inflammation-related disease such as an inflammatory bowel disease particularly ulcerative colitis, and a method for treating an inflammation-related disease in a subject in need thereof.

Therefore, the present disclosure includes at least the following technical solutions.

In one aspect of the present disclosure, provided in embodiments is a biologically pure *Faecalibacterium butyricigenerans* strain AF52-21, deposited under CGMCC Accession No. 1.5206.

In another aspect of the present disclosure, provided in embodiments is a composition, including the biologically pure *Faecalibacterium butyricigenerans* strain AF52-21, and a carrier.

In some embodiments of the present disclosure, the composition is a food composition, or a pharmaceutical composition.

In one embodiment of the present disclosure, the composition is the food composition and the composition further includes a raw-food material or a food additive.

In another embodiment of the present disclosure, the raw-food material or the food additive includes one or more of milk, sugar and vitamins.

In one embodiment of the present disclosure, the composition is the pharmaceutical composition and the composition further includes a pharmaceutically acceptable excipient.

In another embodiment of the present disclosure, the pharmaceutically acceptable excipient includes one or more of lactose, yeast powder, peptone, starch and vitamins.

In one embodiment of the present disclosure, the pharmaceutical composition is an oral formulation.

In another embodiment of the present disclosure, the oral formulation is in a form selected from the group consisting of solution, suspension, emulsion, powder, tablet, pill, syrup, lozenge, troche, chewing gum, capsule and a combination thereof.

In still another aspect of the present disclosure, provided in embodiments is a method for treating an inflammation-related disease in a subject in need thereof, including orally administrating a composition comprising an therapeutic effective amount of *Faecalibacterium butyricigenerans* AF52-21 deposited under CGMCC Accession No. 1.5206, to the subject in need thereof.

In one embodiment of the present disclosure, the inflammation-related disease is the inflammatory bowel disease such as ulcerative colitis.

In another embodiment of the present disclosure, after the administration, a body weight of the subject is increased and/or a weight loss of the subject is mitigated.

In still another embodiment of the present disclosure, after the administration, a disease and activity index (DAI) of the subject is decreased and/or a DAI increase of the subject is suppressed.

In yet another embodiment of the present disclosure, after the administration, mortality of the subject suffering from ulcerative colitis is reduced.

In yet another embodiment of the present disclosure, after the administration, a length of colon is increased and/or a shortening colon length is inhibited.

In yet another embodiment of the present disclosure, the ulcerative colitis is characterized by inflammatory mucosa; a large number of inflammatory cells infiltrating in mucosa, submucosa and even muscularis; bleeding; edema; telangiectasia; and disordered and fractured tissue structure.

In still yet another embodiment of the present disclosure, after the administration, the number of inflammatory cells infiltrating in submucosa is reduced; the number of goblet cells is increased; and gland arrangement is improved.

In still yet another embodiment of the present disclosure, the *Faecalibacterium butyricigenerans* AF52-21 is capable of producing organic acids, wherein the organic acids is short-chain fatty acids (SCFA) comprising one or more of formic acid, acetic acid and butyric acid.

In still yet another embodiment of the present disclosure, the *Faecalibacterium butyricigenerans* AF52-21 is capable of producing organic acids, wherein the organic acids is one or more of 3-methylbutyric acid, valeric acid, quinic acid, lactic acid, oxalic acid, malonic acid, benzoic acid, maleic acid, succinic acid, (trans-)fumaric acid, malic acid, adipic acid, tartaric acid, shikimic acid, citric acid, isocitric acid and L-ascorbic acid.

In still yet another embodiment of the present disclosure, the *Faecalibacterium butyricigenerans* AF52-21 is capable of producing extracellular polysaccharides.

DEPOSIT INFORMATION

Identification reference given by the depositor: AF52-21
Taxonomic Designation: *Faecalibacterium butyricigenerans*
Deposit date: Jun. 13, 2016
Depositary Authority: China General Microbiological Culture Collection Center (CGMCC)
Accession number: CGMCC 1.5206
Address of the depositary authority: No. 3, Yard No. 1, Beichen West Road, Chaoyang District, Beijing, China, 100101.

BRIEF DESCRIPTION OF THE DRAWINGS

The above and/or additional aspects and advantages of the present disclosure will become apparent and easily understood from the description of embodiments in combination with the accompanying drawings, in which.

DETAILED DESCRIPTION

Figure 1:
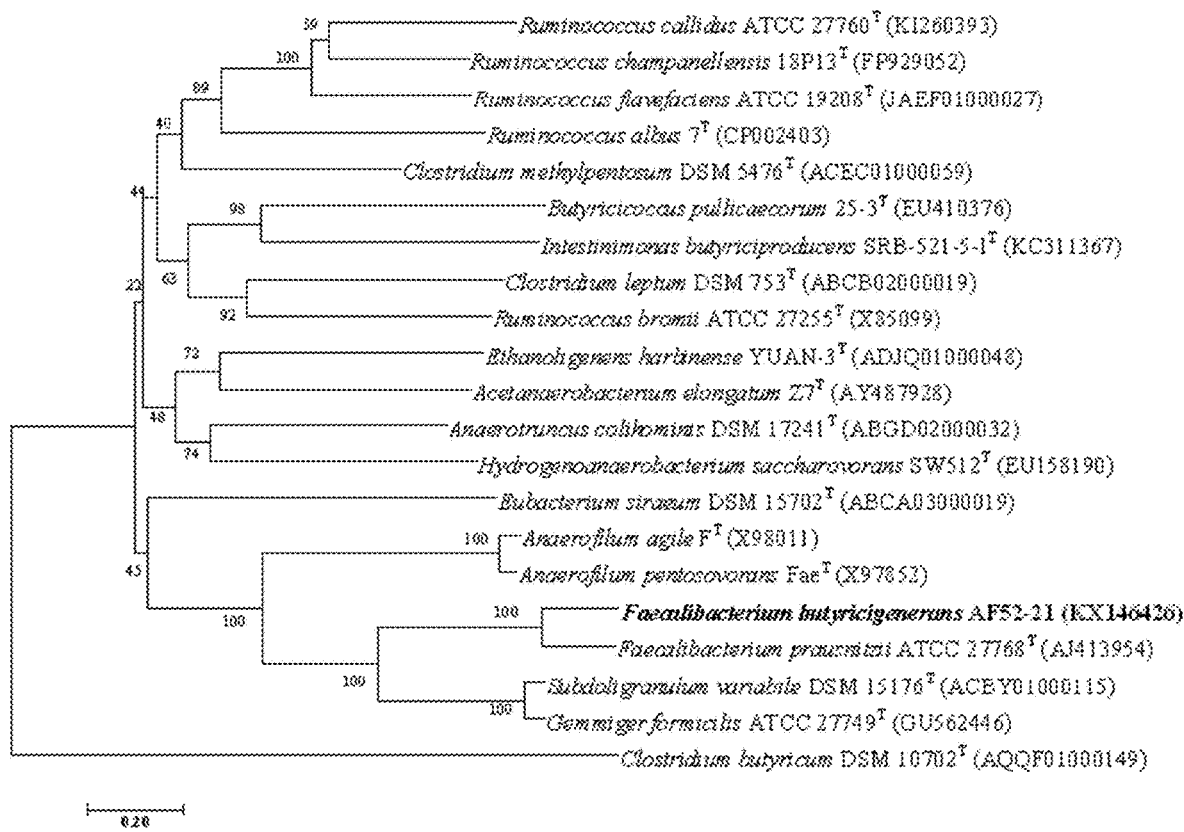
FIG. 1 shows a phylogenetic tree plotted by the maximum likelihood method based on the 16S rDNA sequences of *Faecalibacterium butyricigenerans* in an embodiment of the present disclosure.

Specific description will be made below for the present disclosure with reference to the accompanying drawings.

Example 1: Screening and Identification of *Faecalibacterium butyricigenerans* AF52-21

1.1 Isolation of *Faecalibacterium butyricigenerans* AF52-21
1.1.1 Sample Collection
The sample for isolation was obtained from a stool sample of a healthy male in Shenzhen, China, which is located at 37° 35'37"N and 114° 15'32"E.
1.1.2 Preparation of Medium
The medium used for isolation is an anaerobic PYG medium with a pH value of 6.8-7.0 and a formula of 5 g peptone, 5 g trypticin, 10 g yeast powder, 5 g beef extract, 5 g glucose, 2 g $K_2HPO_4$, 1 mL Tween 80, 0.5 g Cysteine-HCl.$H_2O$, 0.25 g sodium sulfide, 5 mg hemoglobin, 1 μL vitamin $K_1$, 40 mL inorganic salt solution (containing 0.25 g $CaCl_2.2H_2O$, 0.5 g $MgSO_4.7H_2O$, 1 g $K_2HPO_4$, 1 g $KH_2PO_4$, 10 g $NaHCO_3$ and 2 g NaCl per liter), 1 mg resazurin and 950 mL distilled water. The medium with addition of 1.5% agar was sterilized at 115° C. for 25 min, followed by poured into a culture plate in an anaerobic chamber, with a solid medium plate obtained.

1.1.3 Culture for Isolation
The process of culture for isolation was performed under a strict anaerobic condition. In the anaerobic chamber, 0.2 g of the sample collected in 1.1.1 was suspended in a sterilized phosphate buffer solution (PBS) by thoroughly mixing, before 100 μL of the bacterial suspension in a dilution of $10^8$ after a series of 10-fold gradient dilutions was spread onto the solid medium plate obtained in 1.1.2 for incubation at 37° C. After 4 days, a single colony was picked to be streaked on a fresh solid medium plate for further isolation and purification under the same culture condition, thereby obtaining a pure strain for deposit and 16S rDNA identification.

1.2 16S rDNA Identification of *Faecalibacterium butyricigenerans* AF52-21
1.2.1 Extraction of Genomic DNA
The pure strain isolated in 1.1.3 was further cultured until reaching to a bacterial concentration of $10^8$ cfu/ml, 2 ml of which was subjected to genomic DNA extraction.
1.2.2 PCR Amplification of 16S rDNA
The genomic DNA extracted in 1.2.1, as a template, was amplified for 16S rDNA, with a pair of 16S rDNA-targeting universal primers: 8F-1492R. The specific sequences for the primers are as follows:

```
                                          (SEQ ID NO: 1)
     5'-AGAGTTTGATCATGGCTCAG-3';

(SEQ ID NO: 2)
     5'-TAGGGTTACCTTGTTACGACTT-3'.
```

The PCR amplification was conducted as: 94° C. for 4 min; 20 cycles of 94° C. for 30 s, 65° C.-57° C. for 40 s, 72° C. for 90 s; 10 cycles of 94° C. for 30 s, 57° C. for 40 s, 72° C. for 90 s; 72° C. for 10 min; and 4° C. forever.

1.2.3 Purification and Sequencing
The amplified product obtained in 1.2.2 was purified with magnetic beads and then detected by electrophoresis, with a band corresponding to 1.5 kb shown for 16S rDNA. The purified product was then sequenced.

1.2.4 Alignment of 16S rDNA in Database
A near full-length in approximate 1.4 kb of 16S rDNA was determined from sequencing, shown as SEQ ID NO: 3. With alignment in the EzTaxon-e database for the determined sequence of 16S rDNA, preliminary information regarding species taxonomy was determined for the isolated strain, where *Faecalibacterium prausnitzii* ATCC 27768 is the species having 16S rDNA with the highest identity (97.18%) to that of strain AF52-21. Accordingly, it can be preliminarily determined that the strain AF52-21 is a new species belonging to the genus *Faecalibacterium*.

1.3 Phylogenetic Analysis for 16S rDNA of Strain AF52-21
By aligning 16S rDNA of the strain AF52-21 in the EzTaxon-e database, the species with a close genetic relationship to AF52-21 was determined, which were further subjected to sequence alignment for 16S rDNA to that of AF52-21 using Mega5 software, thus obtaining a phylogenetic tree plotted by the maximum likelihood method (FIG. 1). Accordingly, it is determined from the phylogenetic tree that AF52-21 is classified as genus *Faecalibacterium* and the *Faecalibacterium prausnitzii* ATCC 27768 is the species with the closest genetic relationship to AF52-21.

1.4 Microbiological Characteristics of AF52-21

1.4.1 Morphological Characteristics

Figure 2:
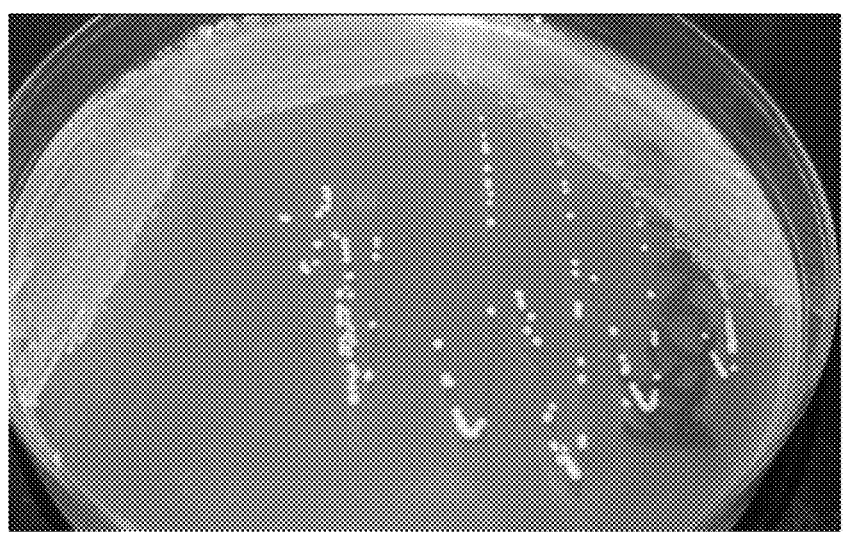
FIG. 2 is a picture showing colonies of *Faecalibacterium butyricigenerans* after cultured for 3 days in an embodiment of the present disclosure.

AF52-21 was cultured in an anaerobic environment at 37° C. for 2-3 days, obtaining a colony grown in non-transparent yellowish-white color, in a sticky state, and in a round bulge shape with a diameter of about 2 mm (FIG. 2).

1.4.2 Microscopic Characteristics

Figure 3:
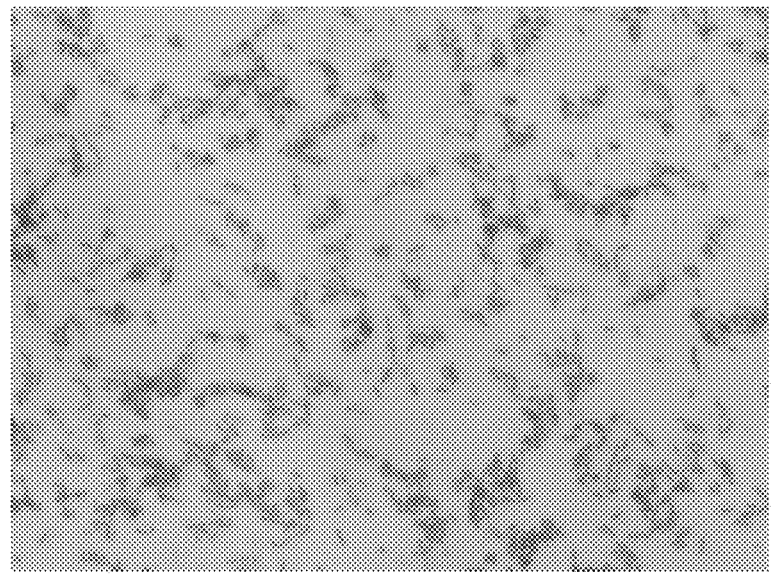
FIG. 3 is a microscope picture (1000×) showing Gram-positive *Faecalibacterium butyricigenerans* in an embodiment of the present disclosure in an embodiment of the present disclosure.

Under a microscope with 1000× magnification, AF52-21 is shown as Gram-negative and in a shape of rod with a diameter of about 1 μm and a length of 2-4 μm; as well lack of spores and flagella (FIG. 3).

1.4.3 Physiological-Biochemical Characteristics

AF52-21 is negative for both oxidase and catalase reactions.

AF52-21 could grow at a temperature ranging from 20–42° C. under a pH value ranging from 6.5-7.5, with the optimal temperature of 37° C. and the optimal pH value of 7.0.

AF52-21 is shown to be tolerant to 1% NaCl.

The comparisons between AF52-21 and the reference strain ATCC 27768 (with the closest genetic relationship to AF52-21) for physiological-biochemical reactions (including substrate utilization API 20A and enzyme reaction API ZYM) are shown in Table 1 as below (with "+" indicating a positive reaction; "-" indicating a negative reaction; and "w" indicating a weak positive reaction).

TABLE 1

| Substrate | AF52-21 | ATCC 27768 |
|---|---|---|
| API 20A | | |
| Tryptophan (Indole generation) | − | − |
| Urea (urease) | − | − |
| Glucose | − | − |
| Mannitol | − | − |
| Lactose | + | − |
| Sucrose | − | − |
| Maltose | − | − |
| Salicyl alcohol | − | − |
| Xylose | − | − |
| Arabinose | − | − |
| Gelatin hydrolysis | − | − |
| Heptaphyllum/ferric citrate | + | + |
| Glycerin | − | − |
| Cellobiose | − | − |
| Mannose | + | − |
| Melezitose | − | − |
| Raffinose | − | − |
| Sorbitol | − | − |
| Rhamnose | − | − |
| Trehalose | + | − |
| API ZYM | | |
| Control | − | − |
| Alkaline phosphatase | − | − |
| Esterase (C4) | − | − |
| Lipid esterase (C8) | − | − |
| Lipase (C14) | − | − |
| Leucine aromaminase | − | − |
| Valine aromaminase | − | − |
| Cystine aromaminase | w | − |
| Trypsin | − | − |
| Chymotrypsin | − | − |
| Acid phosphatase | + | − |
| Naphthol-AS-BI-phosphohydrolase | + | + |
| α-galactosidase | − | − |
| β-galactosidase | − | w |
| β-glucuronidase | + | + |
| α-glucosidase | − | + |
| β-glucosidase | + | − |
| N-acetyl-glucosamine | − | − |
| α-mannosidase | − | − |
| β-fucosidase | − | − |

It can be seen from Table 1 that AF52-21 is significantly different from the reference strain ATCC 27768 in terms of utilization of lactose, mannose and trehalose; and activities of cystine aromaminase, acid phosphatase, β-galactosidase, α-glucosidase and β-glucosidase. Therefore, it has been proven that AF52-21 is a new species different from the known bacteria strain ATCC 27768.

1.5 Analysis for Cellular Fatty Acids

The cultured AF52-21 and reference strain ATCC 27768 in a stationary phase were collected separately for extraction and detection of cellular fatty acids. These two bacterial strains were analysed by gas chromatography for compositions and corresponding amounts of various cellular fatty acids, with the results shown in Table 2 as below.

TABLE 2

| Fatty acids | Name | AF52-21 | ATCC 27768 |
|---|---|---|---|
| $C_{12:0}$ | saturated $C_{12}$ fatty acid | 1.48 | 1.92 |
| $C_{13:1}$ | monounsaturated $C_{13}$ fatty acid | 0 | 1.25 |
| $C_{14:0}$ | saturated $C_{14}$ fatty acid | 5.88 | 11.80 |
| $C_{13:0}$ 3OH/$C_{15:1}$ i I | saturated 3-hydroxyl-$C_{13}$/Type I-monounsaturated iso-$C_{15}$ fatty acid | 0 | 2.14 |
| $C_{16:1}$ ω7c/$C_{16:1}$ ω6c | monounsaturated ω7c/ω6c-$C_{16}$ fatty acid | 1.48 | 4.02 |
| $C_{16:0}$ | saturated $C_{16}$ fatty acid | 16.33 | 21.07 |
| $C_{17:1}$ iso I/anteiso B | Type I-iso/Type B-unsaturated anteiso-$C_{17}$ fatty acid | 4.68 | 7.63 |
| $C_{17:1}$ ω8c | monounsaturated ω8c-$C_{17}$ fatty acid | 1.28 | 1.12 |
| $C_{18:0}$ antei/$C_{18:2}$ ω6, 9c | saturated anteiso -$C_{18}$ fatty acid/diunsaturated ω6, 9c-$C_{18}$ fatty acid | 0 | 1.31 |
| $C_{18:1}$ ω9c | diunsaturated ω9c-$C_{18}$ fatty acid | 39.02 | 31.42 |
| $C_{18:1}$ ω7c | diunsaturated ω7c-$C_{18}$ fatty acid | 8.10 | 5.74 |
| $C_{18:0}$ | saturated $C_{18}$ fatty acid | 4.45 | 4.11 |
| $C_{19:1}$ iso I | Type I-monounsaturated iso-$C_{19}$ fatty acid | 1.19 | 2.12 |
| $C_{19:0}$ iso | saturated iso-$C_{19}$ fatty acid | 12.88 | 0 |
| $C_{18:1}$ 2OH | diunsaturated 2-hydroxyl-$C_{18}$ fatty acid | 2.90 | 1.95 |

Based on the above analysis on phenotype, 16S rDNA sequence and physiological-biochemical reactions, AF52-21 is proved as a new species, which is named as *Faecalibacterium butyricigenerans*.

Example 2: Detection of Bioactive Substances Produced by *Faecalibacterium butyricigenerans* AF52-21

2.1 Detection of Short-Chain Fatty Acids (SCFA)

2.1.1 Sample Preparation 1 ml of AF52-21 bacterial suspension after cultured for 48 hours was centrifuged at 12000 r/min for 5 min, with supernatant collected to be used.

2.1.2 Determination of SCFA

SCFA was assayed by the external standard method, where acetic acid, propionic acid, butyric acid and valeric acid were used to prepare a standard curve. Analysis was performed by means of Gas Chromatograph (GC-7890B, Agilent) equipped with a capillary column (HP-INNOWax (Cross-Linked PEG), 30 m×0.25 mm×0.25 μm) and a hydrogen flame ion detector. The parameters for Gas Chromatograph were set as follows: a column temperature of 180-200° C.; a gasification chamber temperature of 240° C.; a detection temperature of 210° C.; an injection volume of 2 μL; a carrier gas flow rate of 50 mL N2/min; a hydrogen flow rate of 50 mL/min; and an air flow rate of 600-700 mL/min.

2.1.3 Results

The SCFA yield was determined as 4.86 mmol/L of formic acid, 69.7 mmol/L of acetic acid and 15.08 mmol/L of butyric acid.

2.2 Detection of Organic Acids 2.2.1 Sample Preparation

The method is the same as the description for 2.1.1.

2.2.2 Determination of Organic Acids

A standard for detection of organic acids was selected from: 3-methylbutyric acid, valeric acid, quinic acid, lactic acid, oxalic acid, malonic acid, benzoic acid, maleic acid, succinic acid, (trans-)fumaric acid, malic acid, adipic acid, tartaric acid, shikimic acid, citric acid, isocitric acid and L-ascorbic acid. Analysis was performed by means of Gas Chromatograph (GC-7890B, Agilent) equipped with the 122-5532G DB-5 ms column (40 mx0.25 mmx0.25 μm). The parameters for Gas Chromatograph were set as follows: a column temperature of 270-290° C.; an inlet temperature of 250° C.; and a gas flow rate of 0.86 mL/min.

2.2.3 Results

The organic acid yield was determined as the following table (Table 3).

TABLE 3

| Organic acids | | | | | |
| --- | --- | --- | --- | --- | --- |
| 3-methylbutyric acid | valeric acid | quinic acid | lactic acid | oxalic acid | malonic acid |
| Content (mmol/L) 0.38 | 0.39 | 0 | 29.25 | 0 | 0 |

| Organic acids | | | | | |
| --- | --- | --- | --- | --- | --- |
| benzoic acid | maleic acid | succinic acid | (trans-)fumaric acid | malic acid | adipic acid |
| Content (mmol/L) 1.43 | 0.04 | 0.70 | 0 | 0 | 0.80 |

| Organic acids | | | | |
| --- | --- | --- | --- | --- |
| tartaric acid | shikimic acid | citric acid | isocitric acid | L-ascorbic acid |
| Content (mmol/L) 0 | 0 | 0.01 | 0 | 0.11 |

Example 3: Detection of Extracellular Polysaccharides Produced by *Faecalibacterium butyricigenerans* AF52-21

The extracellular polysaccharides were assayed by the phenol sulphate method, where a chromogenic reaction occurs between phenol sulphate and hexoses of free monosaccharides, oligosaccharides and polysaccharides. The absorbance at 490 nm is proportional to the concentration of the extracellular polysaccharide. Specific procedure is as follows:

3.1 Extraction of Extracellular Polysaccharides

After the strain isolated in 1.1.3 was cultured in the PYG medium (prepared as the formula described in 1.1.2 of Example 1) for 2 days, 10 ml of the bacterial suspension was boiled in a water bath for 30 min before centrifuged at 10,000 r/min, with the resulting supernatant collected and added with 80% trichloroacetic acid to a final concentration of 8% for protein precipitation at 4° C. overnight. Afterwards, the supernatant without protein precipitate was centrifuged at 10,000 r/min again for 30 min, with the newly-obtained supernatant collected, adjusted with a pH value of 6.0 using NaOH solution and then added with absolute ethanol (in a volume two times of the supernatant) for polysaccharides precipitation at 4° C. overnight. Then, the centrifugation was performed at 10,000 r/min once again for 30 min, with the supernatant discarded and the pellet dissolved in preheated distilled water for ultrafiltration in an ultrafiltration tube (with a cut-off value of 3000 Da) at 5000r/min for 30 min, such that extracellular polysaccharides were retained on the ultrafiltration membrane in the ultrafiltration tube, which were dissolved in 10 ml distilled water in a volumetric flask, thus obtaining a extracellular polysaccharides solution for use.

3.2 Establishment of a Standard Curve for Glucose

Precisely weighted 20 mg standard glucose was dissolved with distilled water in a 100 ml volumetric flask, from which glucose standard solutions in respective concentrations of 20, 40, 60, 80 and 100 μg/ml were prepared for use. 400 μL standard solutions for each concentration in triplicates were successively added with 400 μL of 5% phenol and 1 ml of concentrated sulfuric acid for reaction. After boiled in a water bath for 15 min and then cooled to room temperature, the resulting solutions were assayed for absorbance at 490 nm. Afterwards, a standard curve was plotted with the absorbance as the ordinate and the concentrations of glucose standard solutions as the abscissa.

3.3 Concentration Assay for the Extracellular Polysaccharides

400 μL of the extracellular polysaccharide solution obtained in 3.1 was successively added with 400 μL of 5% phenol and 1 ml of concentrated sulfuric acid for reaction. After boiled in a water bath for 15 min and then cooled to room temperature, the resulting solution was assayed for absorbance at 490 nm. The concentration was calculated according to the standard curve for glucose.

3.4 Results

After calculation, the extracellular polysaccharide in the *Faecalibacterium butyricigenerans* AF52-21 suspension after cultured for 2 days is in a concentration of 278 mg/L.

Example 4: In Vivo Experiment for *Faecalibacterium butyricigenerans* AF52-21 in a UC Animal Model This example mainly demonstrates the therapeutic effect of *Faecalibacterium butyricigenerans* AF52-21 on UC modeled mice. With administration of AF52-21, saline or a positive drug, the therapeutic effect of *Faecalibacterium butyricigenerans* AF52-21 on the UC modeled mice was evaluated by observing body weight, mortality, fecal traits, occult/visual blood in stool, colon length, disease and activity index (DAI) and pathological parameters.

4.1 Establishment of UC Modeled Mice 8 week-old C57bl/6 mice weighted 21 g±1 g in SPF grade were adaptively fed for one week. Then, 2% sodium dextran sulfate (DSS) was administered to the mice for 7 days to induce the UC modeled mice.

4.2 Grouping

A total of 48 mice were randomly divided into four groups, with 12 mice in each group. The groups were as follows:

Group I: control group—normal mice without DSS induction;

Group II: UC modeled group—saline gavage after DSS induction;

Group III: UC treatment group—AF52-21 treatment after DSS induction;

Group IV: UC treatment group—positive drug (salicylazosulfapyridine, SASP) treatment after DSS induction.

4.3 Administration Scheme

UC modeled group: gavage with saline (0.85% NaCl).

AF52-21-treated group: administration with cultured AF52-21 in a stationary phase in a bacterial concentration of about $10^8$ cfu/ml.

SASP-treated group: administration with 0.02 g/mL of aqueous SASP solution.

4.4 Experimental Procedure

The mice in all groups were daily observed for food intake, spontaneous activities, body weight, fecal traits and occult/visual blood in stool. After DSS induction for 7 days, mice were treated according to the administration scheme in 4.3 for 2 weeks by daily gavage of 200 μL/mouse. After 14 days, mice in all groups were sacrificed for blood collection, colon collection for photographing and length-measuring, and collection of other organs for weighing. The colon was then stored in paraformaldehyde in a −80° C. refrigerator.

4.5 Evaluation of Disease and Activity Indexes (Score of DAIs)

The mice were given individual scores according to body weight, fecal traits and occult/visual blood in stool. The scoring criteria are as follows (Table 4).

TABLE 4

| Weight loss (%) | Fecal traits | Occult/visual blood in stool | Score |
|---|---|---|---|
| 0 | normal | normal | 0 |
| 1-5 | | | 1 |
| 5-10 | loose | positive for occult blood in stool | 2 |
| 10-15 | | | 3 |
| >15 | thin sloppy | visual blood in stool | 4 |

The DAI is scored as the sum of the scores for body weight, fecal traits and occult blood/visual blood in stool.

4.6 Results 4.6.1 Changes in Body Weight

The changes of body weight in different groups before and after DSS induction as well as treatments for different time periods are shown in Tables 5-1 and 5-2.

TABLE 5-1

| Groups | DSS induction at Day 0 (g) | DSS induction at Day 7 (g) | Treatment at Day 1 (g) | Treatment at Day 7 (g) | Treatment at Day 14 (g) |
|---|---|---|---|---|---|
| Control group | 29.34 ± 2.37 | 30.46 ± 2.75 | 30.43 ± 2.33 | 31.07 ± 2.56 | 30.45 ± 2.29 |
| UC Modeled group | 30.28 ± 2.09 | 27.55 ± 3.12 | 25.08 ± 3.27 | 26.90 ± 2.56 | 27.88 ± 1.32 |
| SASP-treated group | 30.12 ± 2.25 | 28.52 ± 3.12 | 26.51 ± 3.31 | 27.60 ± 3.46 | 29.98 ± 3.32 |
| AF52-21-treated group | 30.59 ± 2.10 | 27.28 ± 3.52 | 26.89 ± 3.76 | 28.45 ± 2.76 | 30.29 ± 2.58 |

TABLE 5-2

| Groups | Weight gain/decrease rate | P value (as compared with the UC modeled group) |
|---|---|---|
| Control group | 3 ± 0.7% (gain rate) | 0.008* |
| UC Modeled group | 8 ± 0.8% (decrease rate) | 1 |
| SASP-treated group | 0.4 ± 0.2% (decrease rate) | 0.000* |
| AF52-21-treated group | 0.1 ± 0.1% (decrease rate) | 0.000* |

Table 5-1 shows that the body weight decreased with SSD induction. Table 5-2 shows that the AF52-21 treatment significantly mitigated the loss of body weight as compared with the UC modeled group (* indicating P value <0.05), which was superior to the mitigation caused by the SASP treatment. Therefore, the AF52-21 treatment is better in rescuing the loss of body weight than the SASP treatment.

4.6.2 Score of DAIs

The DAI is scored for all groups at different times of DSS induction for 7 days, treatment for 7 days and treatment for 14 days. Results are shown in Table 6-1 and Table 6-2.

TABLE 6-1

| Groups | DSS induction for 7 days | Treatment for 7 days | Treatment for 14 days |
|---|---|---|---|
| Control group | 2.06 ± 0.51 | 2.28 ± 0.41 | 1.58 ± 0.55 |
| UC modeled group | 7.87 ± 3.22 | 6.56 ± 2.55 | 5.05 ± 1.58 |
| SASP-treated group | 7.70 ± 2.85 | 5.89 ± 2.21 | 3.98 ± 1.38 |
| AF52-21-treated group | 7.79 ± 3.02 | 5.97 ± 2.20 | 3.75 ± 1.67 |

TABLE 6-2

| Groups | Treatment for 14 days | P value (as compared with the UC modeled group) |
|---|---|---|
| Control group | 1.58 ± 0.55 | 0.000* |
| UC modeled group | 5.05 ± 1.58 | 1.000 |
| SASP-treated group | 3.98 ± 1.38 | 0.007* |
| AF52-21-treated group | 3.75 ± 1.67 | 0.003* |

Table 6-1 shows that although slightly decreased over different times after DSS induction, DAIs markedly increased for the UC modeled group as compared to the control group. Table 6-2 shows that the AF52-21 treatment significantly suppressed the increase of DAIs as compared with the UC modeled group (* indicating P value <0.05), which was superior to the suppression caused by SASP treatment. Therefore, the AF52-21 treatment is better in improving DAIs than the SASP treatment.

4.6.3 Mortality Rate

A total of 8 mice died during the entire experiment, with 5 mice died in the UC modeled group, 2 mice died in the SASP-treated group and 1 mouse died in the AF52-21-treated group. Although lacking statistical significance due to the small volume of mice for experiment, the AF52-21 treatment decreased the mortality rate as compared to the UC modeled group.

4.6.4 Changes in Colon Length

Figure 4:
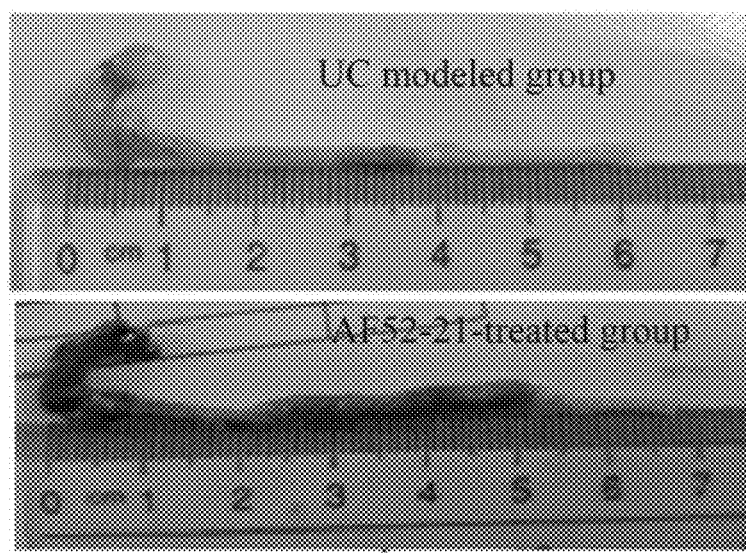
FIG. 4 includes two pictures showing individual colon lengths in a UC modeled group and an AF52-21-treated group in an embodiment of the present disclosure.

For the UC modeled mice, occurrence of ulceration in colon resulted in shortening of the colon length. Results of the colon lengths for the UC modeled group, the SASP-treated group and the AF52-21-treated group are shown in Table 7 and FIG. 4.

TABLE 7

| Groups | colon length | P value (as compared with the UC modeled group) |
| --- | --- | --- |
| Control group | 7.03 ± 0.57 | 0.000* |
| UC modeled group | 6.11 ± 0.90 | 1.000 |
| SASP-treated group | 6.54 ± 0.71 | 0.017* |
| AF52-21-treated group | 6.71 ± 0.87 | 0.029* |

Table 7 shows that the AF52-21 treatment inhibited the shortening of the colon length in the UC modeled group (* indicating P value <0.05), which was superior to the inhibition caused by the SASP treatment. Therefore, the AF52-21 treatment is better in inhibiting the shortening of the colon length than the SASP treatment.

4.6.5 Effect of the AF52-21 Treatment on Organ Index

The organ index, referring to a ratio of organ weight to body weight, indicates general pathological change occurring in the corresponding organ (Table 8).

TABLE 8

| | ($\bar{x}$ ± SD, mg/g) | | | | |
| --- | --- | --- | --- | --- | --- |
| Groups | Colon index | Liver index | Kidney index | Spleen index | Thymus index |
| Control group | 7.08 ± 0.34 | 36.99 ± 4.32 | 13.78 ± 1.64 | 2.36 ± 0.45 | 0.89 ± 0.36 |
| UC modeled group | 10.10 ± 3.01* | 43.64 ± 5.86* | 13.45 ± 1.47 | 6.35 ± 4.47* | 1.69 ± 0.54** |
| SASP-treated group | 9.88 ± 2.76 | 41.56 ± 6.04 | 13.24 ± 1.74 | 6.24 ± 3.71▲ | 1.10 ± 0.39▲ |
| AF52-21-treated group | 8.56 ± 3.21■ | 39.85 ± 5.98■ | 13.57 ± 1.04 | 5.23 ± 4.11■ | 1.53 ± 0.38 |

Table 8 shows that the colon index, the liver index, the spleen index and the thymus index were significantly increased for the UC modeled group as compared with the control group (*/**p<0.05/0.01), suggesting that certain potential pathological changes occurs in colon, liver, spleen and thymus for the UC modeled group. The SASP treatment decreased the spleen index and the thymus index as compared with the UC modeled group (▲p<0.05), indicating that the SASP treatment repairs damages in spleen and thymus to some extents. The AF52-21 treatment significantly decreased the colon index, the liver index and the spleen index as compared with the UC modeled group (■p<0.05), indicating that the AF52-21 treatment markedly repairs damages in colon, liver and spleen, which is superior to the repairs caused by the SASP treatment.

4.6.6 Effect of the AF52-21 Treatment on Colon Histopathology

Figure 5:
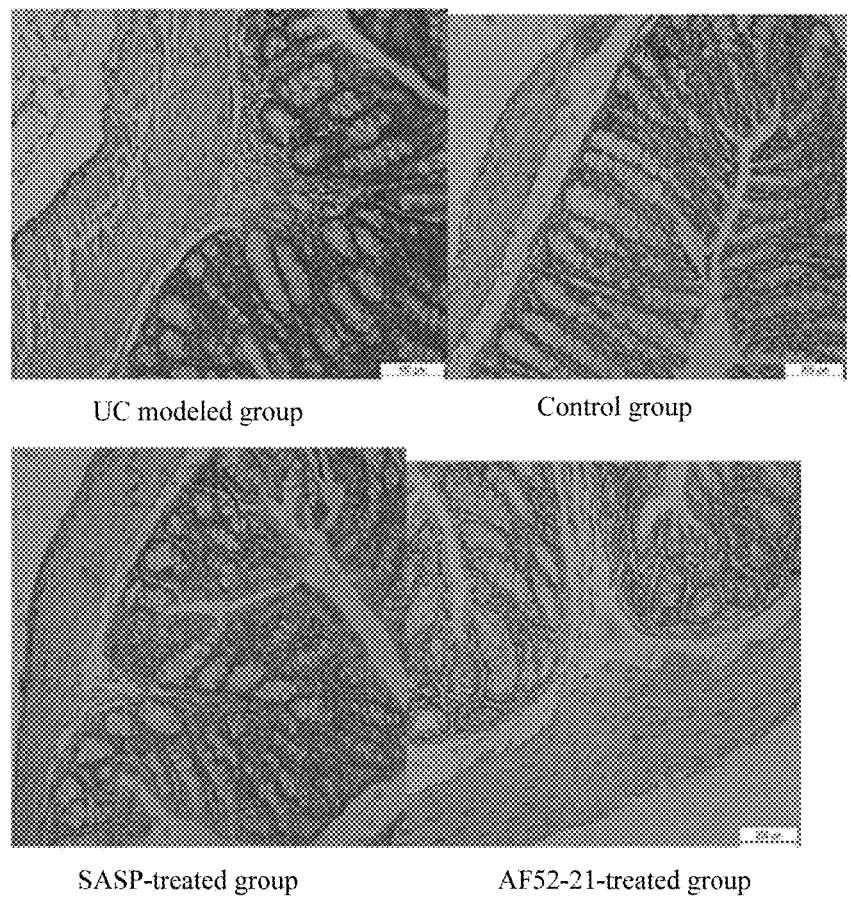
FIG. 5 a picture showing histological sections of mouse intestinal mucosa in a control group, a UC modeled group, an AF52-21-treated group and a SASP-treated group in an embodiment of the present disclosure.

FIG. 5 shows the histopathology changes for colons in different groups. The histopathology picture shows the histopathology for colon in the UC modeled group is characterized by inflammatory mucosa; a large number of inflammatory cells infiltrating in mucosa, submucosa and even muscularis; bleeding; edema; telangiectasia; and disordered and fractured tissue structure. The histopathology picture shows the histopathology for colon in the SASP-treated group is characterized by reduced thickness of colon wall; and reduced number of inflammatory cells infiltrating in submucosa. The histopathology picture shows the histopathology for colon in the AF52-21-treated group is characterized by reduced number of inflammatory cells infiltrating in submucosa; increased number of goblet cells; and well-organized gland arrangement as compared with the UC modeled group. Therefore, the AF52-21 treatment alleviates the pathological changes in the UC modeled group effectively.

Example 5: Food Composition Containing *Faecalibacterium butyricigenerans* AF52-21

Components of a food composition are shown in Table 9 below.

TABLE 9

| Components | Percentage by weight (%) |
| --- | --- |
| *Faecalibacterium butyricigenerans* AF52-21 | 0.5 wt % |
| Milk | 90.0 wt % |
| Sugar | 9.0 wt % |
| Vitamin C | 0.5 wt % |

In accordance with the formula indicated above, the milk and sugar were mixed under stirring to be completely uniform, preheated, homogenized under a pressure of 20 Mpa, sterilized at 90° C. for 5-10 minutes, cooled to 40-43° C., added with vitamin C, and then inoculated with 1-100× $10^6$ cfu/g *Faecalibacterium butyricigenerans* AF52-21, thereby obtaining the food composition containing *Faecalibacterium butyricigenerans* AF52-21.

Example 6: Pharmaceutical Composition Containing *Faecalibacterium butyricigenerans* AF52-21

Components of a pharmaceutical composition are shown in Table 10 below.

TABLE 10

| Components | Percentage by weight (%) |
| --- | --- |
| *Faecalibacterium butyricigenerans* AF52-21 | 1.0 wt % |
| Lactose | 2.0 wt % |
| Yeast powder | 2.0 wt % |
| Peptone | 1.0 wt % |
| Purified water | 93.5 wt % |
| Vitamin C | 0.5 wt % |

In accordance with the formula indicated above, the lactose, yeast powder and peptone were mixed in purified water to be uniform, preheated to 60-65° C., homogenized under a pressure of 20 Mpa, sterilized at 90° C. for 20-30 minutes, cooled to 36-38° C., added with vitamin C, inoculated with viable *Faecalibacterium butyricigenerans* AF52-21 ($1$-$50×10^6$ cfu/mL), fermented at 36-38° C. to achieve a pH value of 6.0, and then centrifuged and freeze-dried to a moisture content less than 3%, thereby obtaining lyophilized *Faecalibacterium butyricigenerans* AF52-21. Afterwards, 0.5 g of the lyophilized *Faecalibacterium butyricigenerans* AF52-21 was mixed with maltodextrin in an equal amount, followed by filling into capsules, thereby obtaining the pharmaceutical composition containing *Faecalibacterium butyricigenerans* AF52-21.

Example 7 Method for Preparing a Medicament for Treating Ulcerative Colitis (UC)

7.1 Preparation of Bacterial Suspension

*Faecalibacterium butyricigenerans* AF52-21 was cultured under an anaerobic condition. The anaerobic medium with reference to that prepared in 1.1.2 was used for fermentation at 37° C. for 2-3 days.

7.2 Preparation of Growth Factors

Skim milk and casein were mixed, followed by centrifugation and ultrafiltration to obtain crude extract of milk growth factors.

7.3 Preparation of Pharmaceutical Formulation

The milk growth factor obtained in 7.2 was mixed with the AF52-21 suspension after fermentation obtained in 7.1 under stirring to be completely uniform, followed by addition of starch as the excipient, thereby obtaining the medicament containing *Faecalibacterium butyricigenerans* AF52-21.

The above examples are further detailed description for the present disclosure in combination with some specific embodiments, which cannot be construed to limit the present disclosure. It will be appreciated for those skilled in the art that simple deductions and alternatives can be made departing from the concept and scope of the present disclosure.

What is claimed is:

1. A method for treating ulcerative colitis in a subject in need thereof, comprising:
    administering an effective amount of isolated *Faecalibacterium butyricigenerans* having a sequence of 16s rDNA of SEQ ID NO: 3 or a composition comprising the *Faecalibacterium butyricigenerans* to the gut of the subject.

2. The method according to claim 1, wherein the *Faecalibacterium butyricigenerans* is *Faecalibacterium butyricigenerans* AF52-21, deposited in the China General Microbiological Culture Collection Center (CGMCC) under the accession No. CGMCC 1.5206.

3. The method according to claim 2, wherein the *Faecalibacterium butyricigenerans* AF52-21 is capable of producing organic acids, wherein the organic acid is short-chain fatty acids (SCFA) comprising one or more of formic acid, acetic acid and butyric acid.

4. The method according to claim 1, wherein after the administration, a body weight of the subject is increased and/or a weight loss of the subject is mitigated.

5. The method according to claim 1, wherein after the administration, a disease and activity index (DAI) of the subject is decreased and/or a DAI increase of the subject is suppressed.

6. The method according to claim 1, wherein after the administration, the mortality of the subject suffering from ulcerative colitis is reduced.

7. The method according to claim 1, wherein after the administration, a length of colon is increased and/or a shortening colon length is inhibited.

8. The method according to claim 1, wherein the ulcerative colitis is characterized by inflammatory mucosa; a large number of inflammatory cells infiltrating in mucosa, submucosa and even muscularis; bleeding; edema; telangiectasia; and disordered and fractured tissue structure.

9. The method according to claim 8, wherein after the administration, the number of inflammatory cells infiltrating in submucosa is reduced; the number of goblet cells is increased; and gland arrangement is improved.

10. The method according to claim 1, wherein the composition is administered orally.

11. The method according to claim 1, wherein the composition is a food composition and the composition further comprises a raw-food material or a food additive; the raw-food material or the food additive comprises one or more of milk, sugar and vitamins.

12. The method according to claim 1, wherein the composition is a pharmaceutical composition and the composition further comprises a pharmaceutically acceptable excipient; the pharmaceutically acceptable excipient is one or more selected from lactose, yeast powder, peptone, starch and vitamins.

13. The method according to claim 12, wherein the pharmaceutical composition is formulated in a form of tablet or capsule.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agagtttgat catggctcag                                                    20

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
tagggttacc ttgttacgac tt                                                 22

<210> SEQ ID NO 3
<211> LENGTH: 1380
<212> TYPE: DNA
<213> ORGANISM: Faecalibacterium butyricigenerans

<400> SEQUENCE: 3
tgcagtcgac gagagagaag gagcttgctt cttcgatcga gtggcgaacg ggtgagtaac        60
gcgtgaggaa cctgcctcaa agaggggac aacagttgga aacgactgct aataccgcat        120
aagcccacgg gtcggcatcg acctgaggga aaaggagcaa tccgctttga gatggcctcg       180
cgtccgatta gctagttggt gaggtaacgg cccaccaagg cgacgatcgg tagccggact       240
gagaggttga acggccacat tgggactgag acacggccca gactcctacg ggaggcagca       300 gtgggaata ttgcacaatg ggggaaaccc tgatgcagcg acgccgcgtg gaggaagaag        360
gtcttcggat tgtaaactcc tgttgttgag gaagataatg acggtactca acaaggaagt       420
gacggctaac tacgtgccag cagccgcggt aaaacgtagg tcacaagcgt tgtccggaat       480
tactgggtgt aaagggagcg caggcgggaa gacaagttgg aagtgaaatc tatgggctca      540
```

```
-continued acccataaac tgctttcaaa actgttttc  ttgagtagtg cagaggtagg cggaattccc   600
ggtgtagcgg tggaatgcgt agatatcggg aggaacacca gtggcgaagg cgggctactg   660
ggcaccaact gacgctgagg ctcgaaagtg tgggtagcaa acaggattag atacctggta   720
gtccacaccg taaacgatga ttactaggtg ttggaggatt gaccccttca gtgccgcagt   780
taacacaata agtaatccac ctggggagta cgaccgcaag gttgaaactc aaaggaattg   840 acggggggccc gcacaagcag tggagtatgt ggtttaattc gacgcaacgc gaagaaccctt  900 accaagtctt gacatccctt gacgaacata gaaatatgtt ttctcttcgg agcaaggaga   960
caggtggtgc atggttgtcg tcagctcgtg tcgtgagatg ttgggttaag tcccgcaacg   1020
agcgcaaccc ttatggtcag ttactacgca agaggactct ggccagactg ccgttgacaa   1080
aacggaggaa ggtggggatg acgtcaaatc atcatgccct ttatgacttg ggctacacac   1140
gtactacaat ggcgttaaac aaagagaagc aagaccgcga ggtggagcaa aactcagaaa   1200
caacgtccca gttcggactg caggctgcaa ctcgcctgca cgaagtcgga attgctagta   1260
atcgtggatc agcatgccac ggtgaatacg ttcccgggcc ttgtacacac cgcccgtcac   1320
accatgagag ccggggggac ccgaagtcgg tagtctaacc gcaaggagga cgccgccgaa   1380
```